United States Patent [19]

Miller et al.

[11] 4,166,107

[45] Aug. 28, 1979

[54] SUSTAINED RELEASE BOLUS FORMULATIONS CONTAINING INSECT GROWTH REGULATORS FOR CONTROL OF LIVESTOCK PESTS

[75] Inventors: John A. Miller; Murray L. Beadles; Roger O. Drummond, all of Kerrville, Tex.

[73] Assignee: The United States of America as represented by the Secretary of Agriculture, Washington, D.C.

[21] Appl. No.: 927,791

[22] Filed: Jul. 25, 1978

[51] Int. Cl.$^2$ .............................................. A61K 9/22
[52] U.S. Cl. .......................................... 424/19; 424/22
[58] Field of Search ..................................... 424/19-22

[56] References Cited

U.S. PATENT DOCUMENTS 3,056,724  10/1962  Marston ................................. 424/22
3,535,419  10/1970  Siegrist et al. ........................ 424/22

OTHER PUBLICATIONS

Miller, J. A.; Beadles, M. L.; Palmer, J. S.; Pickens, M. O.; J. Econ. Entomol. 70(5): 589–591, Oct. 1977, Methoprene for Control of the Horn Fly (*Haematobia irritans*): A Sustained-Release Bolus Formulation for Cattle.

Kunz, S. E.; Bay, D. E.; Southwest Entomol. 2(1): 27–31, Mar. 1977, Diflubenzuron: Effects on the Fecundity, Production and Longevity of the Horn Fly (*Haematobia irritans*).

Gingrich, A. R.; Hopkins, D. E.; J. Econ., Entomol. 70(1): 107–108, Feb. 1977, Stages of the Horn Fly (*Haematobia irritans*) Susceptible to Methoprene.

*Primary Examiner*—Shep K. Rose
*Attorney, Agent, or Firm*—M. Howard Silverstein; David G. McConnell; Salvador J. Cangemi

[57] ABSTRACT

Compositions of insect regulators comprising monostearin, carnuba wax, barium sulfate, methoprene, and diflubenzuron are selectively formulated into a sustained-release bolus and orally administered to livestock to control the larvacidal activity of arthropods in the manure of the livestock.

6 Claims, No Drawings

SUSTAINED RELEASE BOLUS FORMULATIONS CONTAINING INSECT GROWTH REGULATORS FOR CONTROL OF LIVESTOCK PESTS

BACKGROUND OF THE INVENTION

1. Field of the Invention

This invention relates to insect control formulations. More specifically, this invention relates to the control by larvacidal activity of arthropods in the manure of livestock. Even more specifically, this invention relates to the control of arthropods through the formulation of insect growth regulators in a sustained-release bolus form which is orally administered to livestock.

2. Description of the Prior Art

Repeated application of insecticides directly to cattle is currently the most advanced method available to producers for the control of livestock pests. In fact, in the past 25 years, progress in control has been limited primarily to the development of new insecticides. However, the principal problem involved in the control of livestock pests is not unavailability of effective toxicants. Instead, it is the relatively short duration of effectiveness of the available compounds due to photodecomposition, evaporation, and adsorption of the materials, and to mechanical losses caused by rubbing of the animal and self-grooming.

Repeated treatment of livestock is expensive in terms of both labor and insecticide. To compensate for rapid degradation of the pesticides on animals, the producer must apply larger quantities than are necessary for control of the immediate population if toxic levels are to be maintained for any length of time. Such a practice is wasteful of insecticide, results in greater contamination to the environment, and increases the probability of toxicity to animals and of residues in animal products.

Therefore, one of the objectives of studies conducted at the U.S. Livestock Insects Laboratory, Kerrville, Tex., is to develop techniques that will make it possible to maintain the minimum effective level of toxicant on livestock over an extended period and thereby to increase the efficacy, efficiency, and safety of livestock pest control. This report deals with our efforts to use controlled-release technology against horn flies, *Haematobia irritans* (L.), common cattle grubs, *Hypoderma lineatum* (De Villers), and face fly, *Musca autumnalis* (DeGeer).

Boluses have been used in veterinary medicine to provide nutritional and therapeutic substances to animals for predetermined periods. But, for several reasons the technique has not been used in the control of livestock pests: (1) the effective dose of most conventional insecticides is usually too large for the bolus form to be practical; (2) many insecticides are degraded by the digestive processes of the animal and by the environment; and (3) conventional insecticides can accumulate in animal tissues and thereby produce objectionable residues. However, insect growth regulators (IGR's) are chemicals of another type and might be more acceptable in a bolus than conventional insecticides.

Insect growth regulators have been used successfully in the control of dung breeding pests of cattle for several years. Complete inhibition of development in manure has been achieved by administering insect growth regulators (IGR) to cattle in ground feed (Harris et al, 1973), in mineral blocks (Harris et al, 1974) and in drinking water (Beadles et al, 1975; Miller et al, 1976, 1977). Free-choice consumption and the resultant variations in dosage are inherent problems in the practical application of any of these techniques. Additionally, in some areas, animals will not consume supplemental minerals since their mineral requirements are amply met by the natural diet. The presence of untreatable sources of water (streams, rainfall) can interfere with the use of a water treatment.

The use of sustained-release bolus formulations is another approach to supplying animals with small daily dosages of materials. Boluses have been used in animal husbandry to provide nutritional and therapeutic substances such as trace elements, antibiotics, anthelmintics, animal hormones, and growth stimulants over predetermined periods of time. The prior art for these dosages forms is adequately described in patent literature such as, for example, U.S. Pat. No. 3,056,724 (Marston 1962), U.S. Pat. No. 3,507,952 (Rednick and Tucker 1970) and U.S. Pat. No. 3,535,419 (Siegrist and Katz 1970). However, bolus dosage forms have not been used in the control of livestock arthropods because the effective dosage of most conventional insecticides is usually too large to make the bolus form practical, many insecticides are destroyed by digestive process and environment, and conventional insecticides are often accumulated in animal tissues and, thereby produce undesirable residues.

The use of sustained-release bolus formulations to administer insect growth regulators for the control of livestock pests overcomes many of the aforementioned problems associated with ad lib treatments. Additionally, the efficacy and relative safety to insect growth regulators enables the use of the bolus treatment for long-lasting control measures.

An example of a veterinary composition is described in the literature, such as, for example, in U.S. Pat. No. 3,535,419. The patent discloses boluses which provide for the release of a progestational agent over an approx. 30 days for controlling and timing fertility.

SUMMARY OF THE INVENTION

The instant invention can best be described as an effective composition formulated into an orally administered bolus for livestock to control by larvacidal activity certain arthropods in the manure of the livestock. The unique formulation comprises about 4–17 parts by weight monostearin, about 4–10 parts by weight carnuba wax, about 70–75 parts by weight of Barium Sulfate, and about 1–15 parts by weight insect growth regulator.

Definitions of Terms Used

Fistula—passageway installed in the rumen of a cow for observation of the erosion rate of the bolus.
Monostearin—$HOCH_2CH(OH)CH_2O_2C(CH_2)_{16}CH_3$
Carnuba wax—Brasil wax, #1 yellow. A hard brittle high-melting wax from the leaves of the carnauba palm.
Methoprene—isopropyl (E,E)-11 methoxy-3,7,11-trimethyl2,4-dodecadienoate.
Bolus—a rounded mass as a large pill.
Diflubenzuron—N-[[(4-chlorophenyl)amino]carbonyl]-2,6-difluorobenzamide.

DESCRIPTION OF THE PREFERRED EMBODIMENTS

Research by the authors has yielded bolus formulations that release insect growth regulators into the digestive tract of cattle in sufficient quantities for control of flies over a 13–24-week period. The bolus is formulated to have a specific gravity >1.5 in order that it might be retained in the reticulum of the cattle. The digestive activities within the reticulum erode the bolus causing release of the insect growth regulator.

The present invention can best be described as an effective composition for administering insect growth regulators to cattle. The actual preparation can be accomplished with variations. The examples provided are to illustrate preferred embodiments and should not be construed to be all inclusive or as limitations to possible preparations.

Basically, the invention involves a blending of an insect growth regulator with a combination of wax and fat. A high-density insoluble, non-toxic metallic compound is added to the composition both as an inert filler and as a means of increasing the density of the mixture. The formulation is comprised of:

(a) about 4–17 parts by weight monostearin
(b) about 4–10 parts by weight carnuba wax
(c) about 70–75 parts by weight Barium Sulfate
(d) about 1–15 parts by weight insect growth regulator The following table gives examples of particular useful formulations containing methoprene as the active agent:

| Component | % by weight A | B |
|---|---|---|
| Monostearin | 15 | 5 |
| Carnuba wax | 7 | 10 |
| Barium sulfate | 75 | 75 |
| Methoprene | 3 | 10 |

EXAMPLE 1

Boluses were made according to formulation A above. The monostearin and carnuba wax were melted at 100–120° C. and thoroughly blended. The methoprene was then blended into the molten mixture. Next, the barium sulfate was added and blended until a creamy mixture was obtained. The resultant molten material was poured into a preheated (100–120° C.) mold. The mold was set on a vibrating device to allow air bubbles to migrate out of the mixture. The mixture was allowed to cool at room temperature. The resultant boluses, approximately 2.3 cm. dia×7.6 cm length, were then removed from the mold. Each bolus was domed at both ends and the weight adjusted to 80 g.

One of these boluses was administered to a fistulated cow and removed periodically for examination. The erosion rate was observed to decline from 0.1 g/day 13-day posttreatment to 0.08 g/day on the 67-day posttreatment. The manure from the treated animal and an untreated control were bioassayed against the horn fly. Complete inhibition of emergence was observed in the samples from the treated animal whereas 80–90% of the pupa from untreated samples produced adult horn flies.

In order to test the bolus under more natural conditions, a herd of 11 angus cows (approx. 400 kg body wt) were treated with one 80 g bolus each. The samples of manure were collected weekly from this herd and bioassayed against the horn fly. Manure from a untreated herd was also bioassayed for comparisons. Over the first 24-week posttreatment, only 1.8% of the pupa produced in manure from the treated herd produced adults, whereas 91% of the pupa from untreated controls produced adult horn flies. Therefore, the bolus composition successfully metered sufficient methoprene over the 24 weeks to effect a 98% inhibition of horn fly development.

In addition to observations on the horn fly, cattle grubs (*Hypoderma lineatum*), were collected from several of the animals. Of 26 grubs collected from the treated cattle, no adults emerged from the paparium. Those collected from utnreated controls had 70% adult emergence. Therefore, it appears that in addition to larvacidal activity, the 3% methoprene bolus had a systemic effect on cattle grubs.

EXAMPLE 2

Ten percent methoprene boluses were formulated according to B above. The boluses were produced as described in Example 1. One such bolus was installed in a fistulated animal and observations on the rate of disintegration recorded. Over a 20-week period, the weight of the bolus declined from an initial 80 g to 56 g after 5 weeks in the reticulum of the steer, 36 g after 10 weeks, and 10 g after 20 weeks. The disintegration rate appeared to follow an exponential decline. The manure from the treated animal was collected and bioassayed against the stable fly, although the target pest for this formulation is the face fly. Since the face fly does not exist in the vicinity of the U.S. Livestock Insect Laboratory, Kerrville, Tex., and the stable fly has approximately equal susceptibility to methoprene, the stable fly bioassay was used as a model for the face fly.

During the first 15-week posttreatment, 20% of the pupa produced in samples from the treated animal emerged compared to 94% of pupa reared in manure from untreated animal-produced adults. Therefore, the 10% methoprene bolus inhibited stable fly development approximately 79% and would be expected to produce similar results against the face fly.

EXAMPLE 3

| Component | % by weight |
|---|---|
| Monostearin | 13 |
| Carnuba wax | 7 |
| Barium sulfate | 70 |
| Diflubenzuron | 10 |

Boluses were fabricated in a manner similar to that used in Examples 1 and 2 with the components shown above. An 80 g bolus was administered to a 400-kg cow. The manure from this animal was bioassayed against both the horn fly and the stable fly. During the first 13-weeks posttreatment, bioassays against horn fly only were conducted. On the 14th week bioassays against the stable fly were begun. Manure from the treated animal, although showing a gradual increase in the number of pupa produced, did not produce adults of either the horn fly or the stable fly until the 23rd week posttreatment. On the 24th week, the animal was fistulated and a 10-g remnant of the original 80-g bolus was recovered from the reticulum of the cow.

Similar results have been attained by using a compressed rather than a molded bolus of the described formulations. The molten mixture was poured into an open, cooling pan rather than the mold. After cooling and solidifying, the composition was ground in a blender with dry ice to avoid heating and sticking. The material was powdered until it passes through a 30-mesh sieve. The powder was then poured into a mold (2.2 cm dia.×7.6 cm long). The base and the piston of the cylindrical mold are recessed to produce domed ends upon compression.

The powder was slowly compressed end to end to 15,000 psi. Fifty-gram boluses ca. 2.2 cm dia.×5 cm length were produced in this fashion. Cattle treated at the rate of 1 50-g bolus per 200-kg body weight have produced results similar to those described for the 80 g molded boluses.

Release rate can be adjusted by changes in the ratio of monostearin to carnuba wax in the formulation. In general, release rate is increased by an increase in the quantity of monostearin in the formulation and decreased with increases in the quantity of carnuba wax. In addition, changes in the ratio of monostearin and carnuba wax to barium sulfate cause changes in disintegration rate.

A balance must be sought between release rate and concentration of insect growth regulator in the bolus. Decreases in erosion rate in order to increase duration of the bolus must be accompanied by increased in active ingredient to meet effective dosage throughout the desired period of control.

We claim:

1. A sustained release bolus formulation for the control of arthropods in cattle manure, said formulation comprising the following composition: about 4–17 parts monostearin, about 4–10 parts carnuba wax, about 70–75 parts Barium Sulfate, and about 1–15 parts methoprene.

2. The sustained release bolus formulation of claim 1 for the control of horn flies in cattle manure, said formulation comprising the following composition: about 15 parts monostearin, about 7 parts carnuba wax, about 75 parts Barium Sulfate, and about 3 parts Methoprene.

3. The sustained release bolus formulation of claim 1 for the control of grubs in cattle, said formulation comprising the following composition: about 15 parts monostearin, about 7 parts carnuba wax, about 75 parts Barium Sulfate, and about 3 parts Methoprene.

4. The sustained release bolus formulation of claim 1 for the control of the stable fly and the face fly in the manure of the cattle, said formulation comprising the following composition: about 5 parts Monostearin, about 10 parts Carnuba Wax, about 75 parts Barium Sulfate, and about 10 parts Methoprene.

5. A sustained release bolus formulation for the control of arthropods in cattle manure, said formulation comprising the following composition: about 4–17 parts monostearin, about 4–10 parts Carnuba Wax, about 70–75 parts Barium Sulfate, and about 1–15 parts diflubenzuron.

6. The sustained release bolus formulation of claim 5 for the control of the stable fly and the face fly in the manure of the cattle, said formulation comprising the following composition: about 13 parts Monostearin, about 7 parts Carnuba Wax, about 70 parts Barium Sulfate, and about 10 parts diflubenzuran.

* * * * *